(12) United States Patent
Kim et al.

(10) Patent No.: US 11,464,861 B2
(45) Date of Patent: Oct. 11, 2022

(54) PHARMACEUTICAL COMPOSITION WITH IMPROVED STORAGE STABILITY AND METHOD FOR PREPARING THE SAME

(71) Applicant: SAMYANG HOLDINGS CORPORATION, Seoul (KR)

(72) Inventors: Bong Oh Kim, Daejeon (KR); Bum Chan Min, Daejeon (KR); Ji Yeong Kim, Hanam-si (KR); Hye Rim Kim, Daejeon (KR); Min Hyo Seo, Daejeon (KR); Sa Won Lee, Daejeon (KR); Yil Woong Yi, Daejeon (KR); Joong Woong Cho, Daejeon (KR); In Ja Choi, Daejeon (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 0 days.

(21) Appl. No.: 16/857,724

(22) Filed: Apr. 24, 2020

(65) Prior Publication Data
US 2020/0246468 A1 Aug. 6, 2020

Related U.S. Application Data

(63) Continuation of application No. 15/222,157, filed on Jul. 28, 2016, now abandoned.

(60) Provisional application No. 62/198,457, filed on Jul. 29, 2015.

(51) Int. Cl.
| | | |
|---|---|---|
| *A61K 47/34* | (2017.01) | |
| *A61K 9/107* | (2006.01) | |
| *A61K 31/337* | (2006.01) | |
| *A61K 47/32* | (2006.01) | |
| *A61K 9/00* | (2006.01) | |

(52) U.S. Cl.
CPC .......... *A61K 47/34* (2013.01); *A61K 9/0019* (2013.01); *A61K 9/1075* (2013.01); *A61K 31/337* (2013.01); *A61K 47/32* (2013.01)

(58) Field of Classification Search
CPC ...... A61K 31/337; A61K 47/32; A61K 47/34; A61K 9/1075; A61K 9/0019; A61K 31/122; A61K 47/30
See application file for complete search history.

(56) References Cited

U.S. PATENT DOCUMENTS

| | | | |
|---|---|---|---|
| 6,322,805 B1 | 11/2001 | Kim et al. | |
| 6,840,968 B2 * | 1/2005 | Chang | B01D 7/00 23/294 R |
| 7,217,770 B2 * | 5/2007 | Seo | A61K 9/1075 525/419 |
| 8,853,351 B2 | 10/2014 | Kim et al. | |
| 2010/0280214 A1 * | 11/2010 | Kim | C08G 63/664 528/272 |
| 2010/0286075 A1 | 11/2010 | Lee et al. | |
| 2013/0345297 A1 | 12/2013 | Lee et al. | |
| 2016/0137775 A1 | 5/2016 | Ruan et al. | |

FOREIGN PATENT DOCUMENTS

| | | |
|---|---|---|
| CA | 2231886 C | 3/2002 |
| CN | 103601878 A | 2/2014 |
| WO | WO 01/85216 A1 | 11/2001 |
| WO | WO 01/87345 A1 | 11/2001 |

OTHER PUBLICATIONS

Dong et al., "Nanoparticles of poly(D,L-lactide)/methoxy poly(ethylene glycol)-poly(D,L-lactide) blends for controlled release of paclitaxel," Journal of Biomedical Materials Research Part A, 2006, pp. 12-19.
Esmaeili et al., "Folate-receptor-targeted delivery of docetaxel nanoparticles prepared by PLGA-PEG-folate conjugate," Journal of Drug Targeting, vol. 16, Issue 5, 2008, pp. 415-423.
European Search Report for EP Application No. 16830849.2 dated Feb. 12, 2019.
Kim et al., "In vivo evaluation of polymeric micellar paclitaxel formulation: toxicity and efficacy," Journal of Controlled Release, vol. 72, 2001, pp. 191-202.
Ouahab et al., "Development and characterization of stabilized double loaded mPEG-PDLLA micelles for simultaneous delivery of paclitaxel and docetaxel," Drug Development and Industrial Pharmacy, vol. 40, No. 7, 2014 (published online Apr. 19, 2013), pp. 860-868.
Zhu et al., "Preparation, characterization, and properties of polylactide (PLA)-poly(ethylene glycol)(PEG) copolymers: A potential drug carrier," Journal of Applied Polymer Science, vol. 39, 1990, pp. 1-9.

* cited by examiner

*Primary Examiner* — Jean P Cornet
(74) *Attorney, Agent, or Firm* — Birch, Stewart, Kolasch & Birch, LLP

(57) ABSTRACT

A pharmaceutical composition containing a specific related compound within a specified limit and a method for preparing the same are provided.

11 Claims, 5 Drawing Sheets

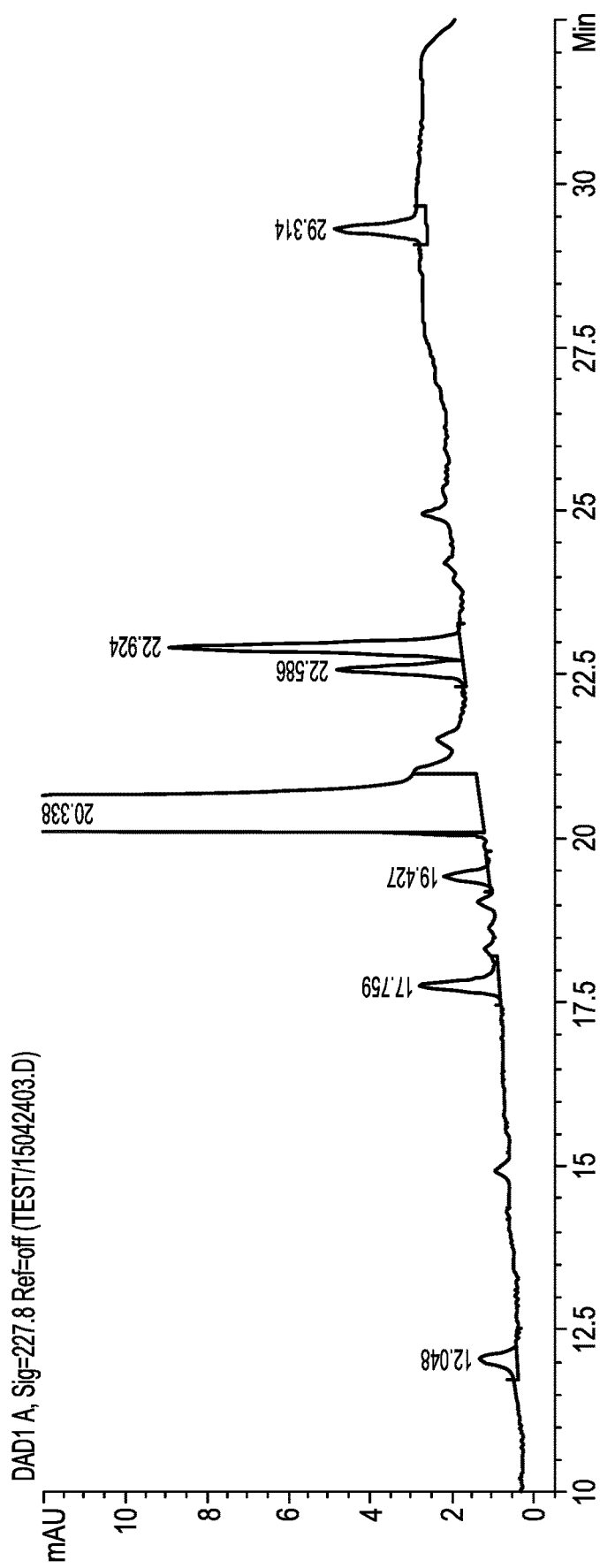
[Figure 1]

[Figure 2]
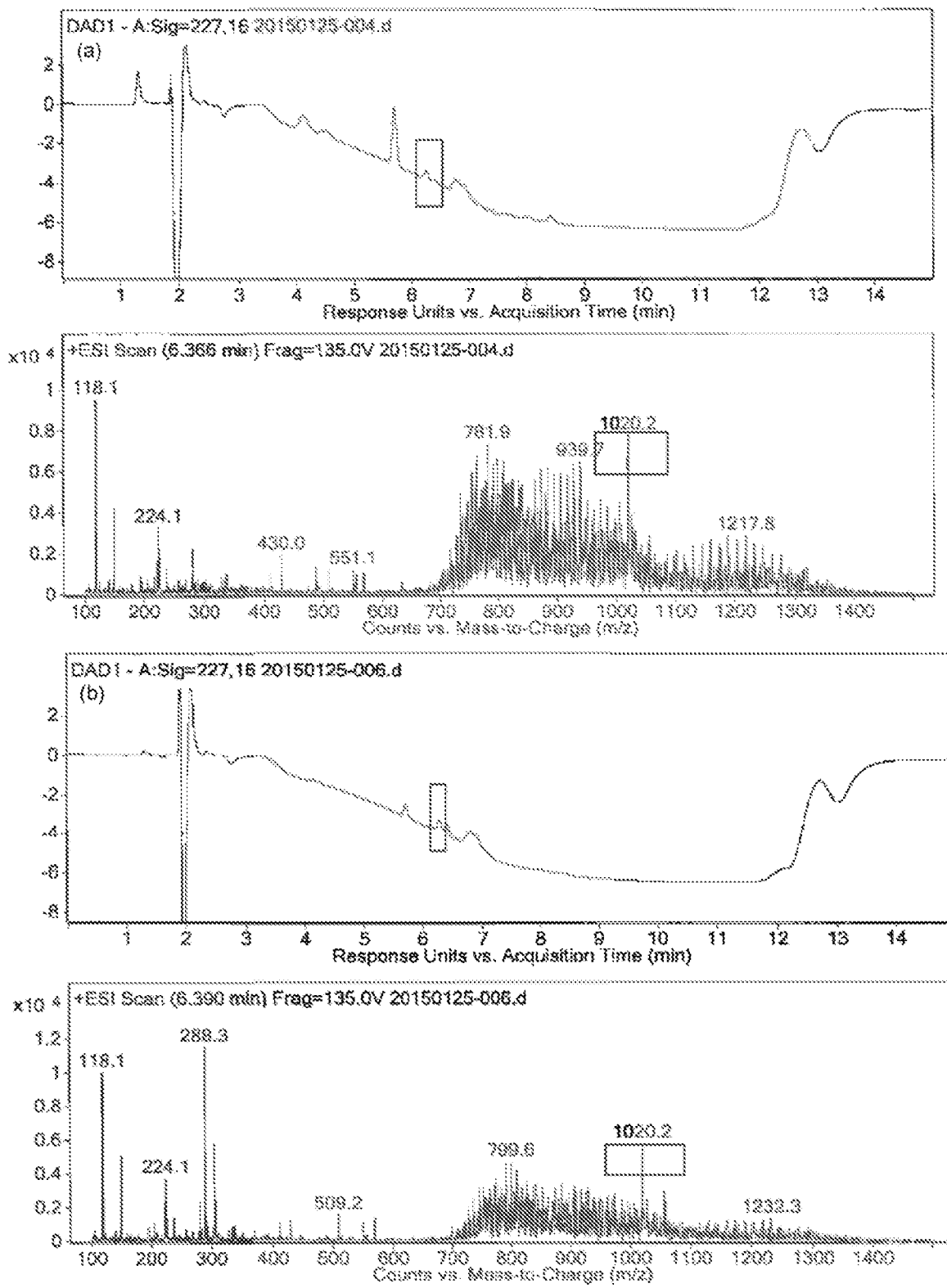

[Figure 3]
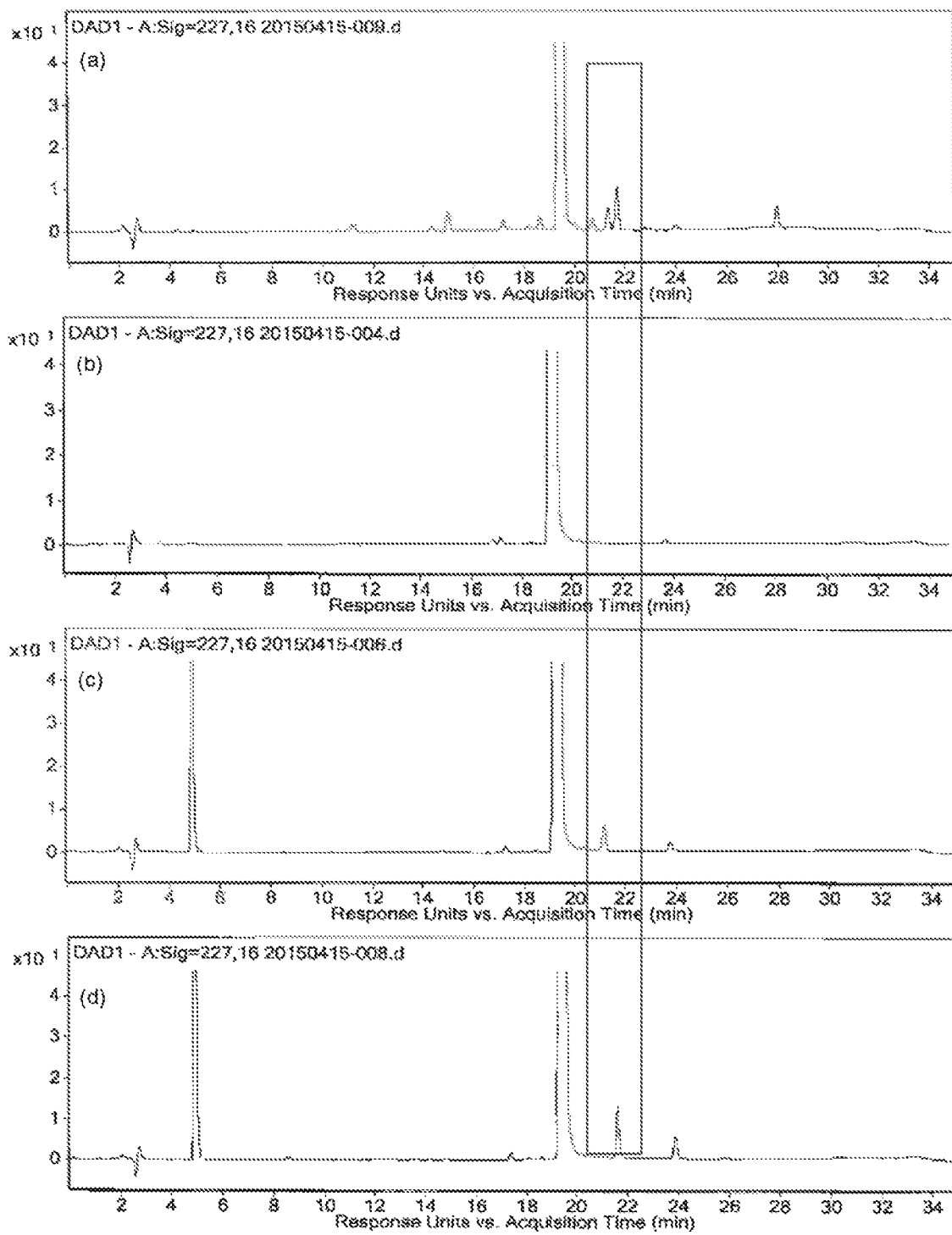

[Figure 4]
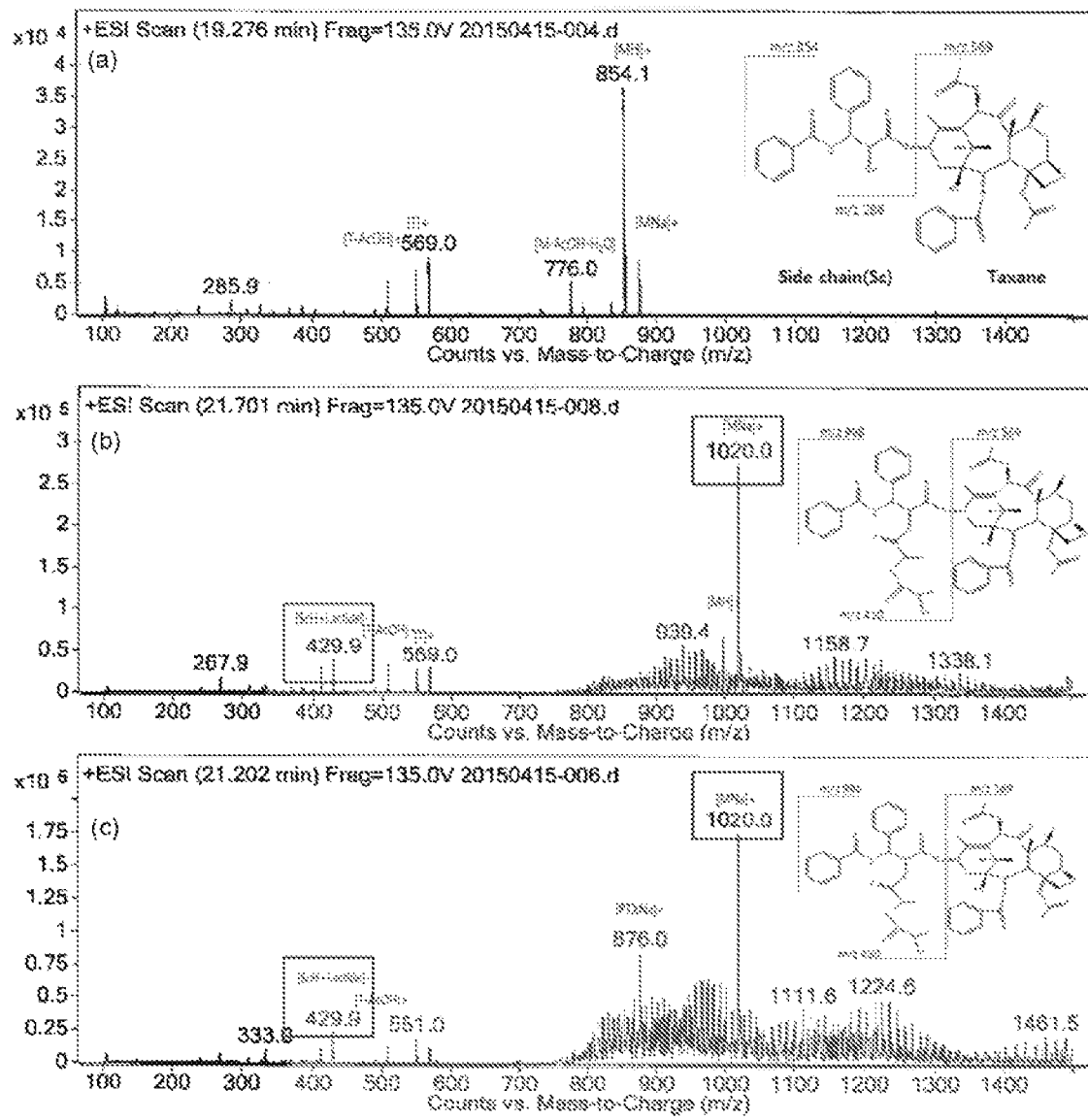

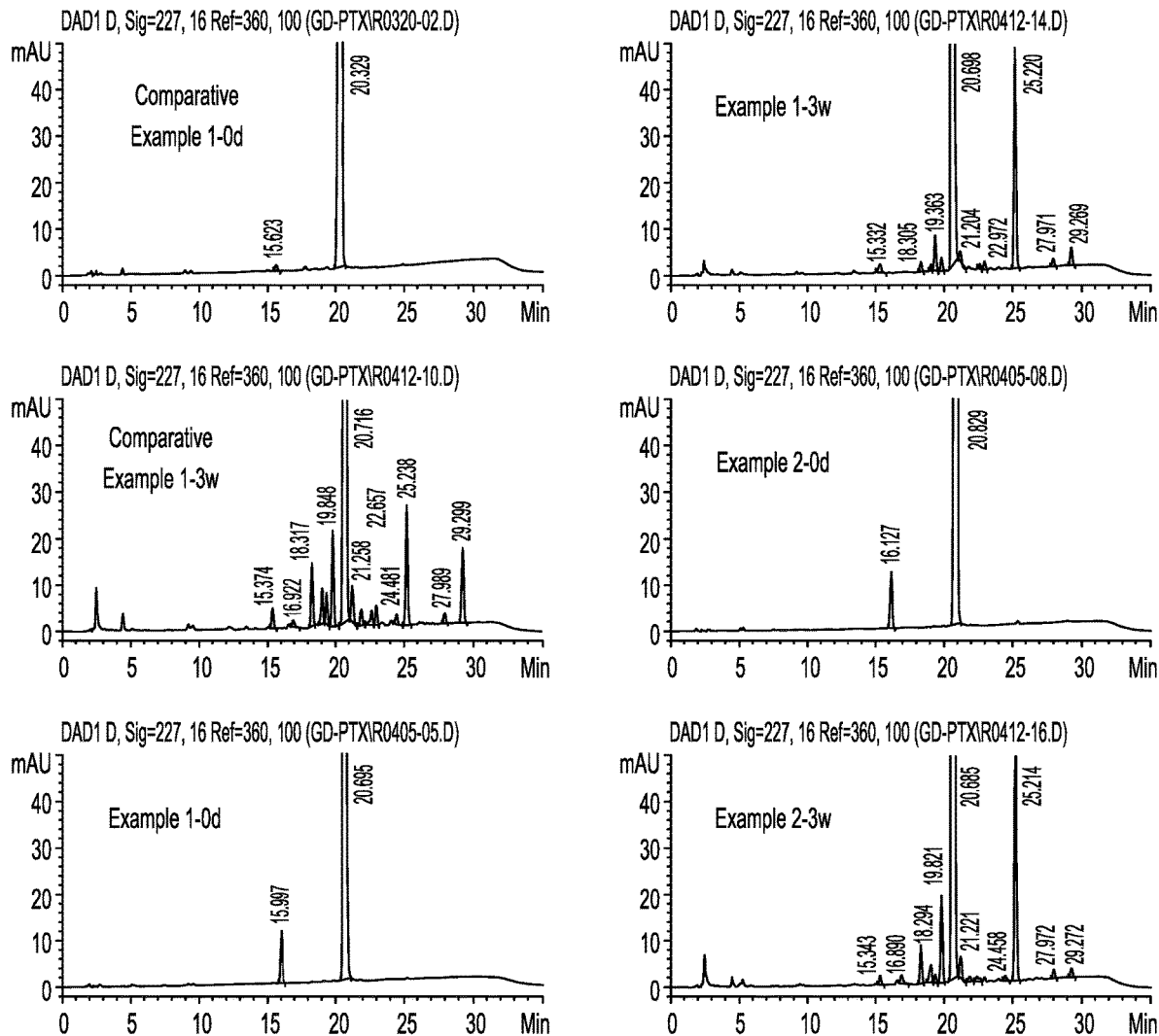
[Figure 5]

PHARMACEUTICAL COMPOSITION WITH IMPROVED STORAGE STABILITY AND METHOD FOR PREPARING THE SAME

CROSS REFERENCE TO RELATED APPLICATIONS

This application is a Continuation of U.S. application Ser. No. 15/222,157, filed on Jul. 28, 2016, which claims the benefit under 35 U.S.C. § 119(e) to U.S. Provisional Application No. 62/198,457, filed on Jul. 29, 2015, the disclosures of all these applications are incorporated herein by reference.

TECHNICAL FIELD

The present disclosure relates to a pharmaceutical composition with improved storage stability and a method for preparing the same, and more specifically, a pharmaceutical composition of poorly water-soluble drug comprising an amphiphilic block copolymer wherein the content of a specific related compound is kept within a specified limit, and a method for preparing the same.

BACKGROUND ART

Solubilization of a poorly water-soluble drug is a key technology for delivering the drug into the body via oral or parenteral administration. Such solubilization methods include a method of adding a surfactant to an aqueous solution to form micelles and then entrapping a poorly water-soluble drug therein. An amphiphilic block copolymer used as a surfactant comprises a hydrophilic polymer block and a hydrophobic polymer block. Since the hydrophilic polymer block directly contacts blood proteins and cell membranes in vivo, polyethylene glycol or monomethoxypolyethylene glycol, etc. having biocompatibility has been used. The hydrophobic polymer block improves affinity to a hydrophobic drug, and polylactide, polyglycolide, poly(lactic-glycolide), polycaprolactone, polyamino acid or poly-orthoester, etc. having biodegradability has been used. In particular, polylactide derivatives have been applied to drug carriers in various forms because they have excellent biocompatibility and are hydrolyzed into harmless lactic acid in vivo. Polylactide derivatives have various physical properties depending on their molecular weights, and have been developed in various forms such as microsphere, nanoparticle, polymeric gel and implant agent.

U.S. Pat. No. 6,322,805 discloses a composition for delivering a poorly water-soluble drug consisting of a polymeric micelle-type drug carrier and a poorly water-soluble drug, wherein the polymeric micelle-type drug carrier is formed from a diblock or triblock copolymer which is not crosslinked by a crosslinking agent and consists of at least one biodegradable hydrophobic polymer selected from the group consisting of polylactide, polyglycolide, poly(lactide-glycolide), polycaprolactone and derivatives thereof and poly(alkylene oxide) as a hydrophilic polymer, wherein the poorly water-soluble drug is physically entrapped in the drug carrier and solubilized, and wherein the polymeric micelle-type drug carrier forms a clear aqueous solution in water and effectively delivers the poorly water-soluble drug into the body. According to the above US patent, polyethylene glycol-polylactide diblock copolymer is synthesized by removing moisture from monomethoxypolyethylene glycol, adding stannous octoate dissolved in toluene thereto and removing toluene under reduced pressure, adding D,L-lactide to the resulting mixture and conducting a polymerization reaction, adding chloroform to dissolve the produced block copolymer, dropwise adding an excess amount of diethyl ether in small portions with stirring to form precipitant and filtering the formed precipitant, and washing it several times with diethyl ether. However, this method is difficult to employ in mass-scale production and thus is not commercially available. In addition, the ether that has been used for purification may remain in the final polymeric micelle composition.

U.S. Pat. No. 8,853,351 discloses a method for preparing an amphiphilic block copolymer, comprising (a) dissolving the amphiphilic block copolymer in a water-miscible organic solvent; (b) adding and mixing an aqueous solution of alkali metal salt (sodium bicarbonate, sodium carbonate, potassium bicarbonate, potassium carbonate or lithium carbonate) to the polymeric solution obtained in step (a); (c) separating organic and aqueous phases by salting out for the solution obtained in step (b); and, (d) isolating the organic phase obtained in step (c) and removing the organic solvent therefrom to recover the polymer. However, the method involves complicated steps, and requires an additional step for removing the alkali metal salt and the salt (sodium chloride or potassium chloride) used for salting out, and may have residual metal salts even after the removal thereof.

Impurities of drug must be strictly controlled in various aspects. Particularly, in case of impurities derived from active pharmaceutical ingredient (API), each country determines in its drug approval guideline the upper limit to amount of API-derived, known or unknown impurities (related compounds) in a drug product. In addition, there are some standards used internationally and ICH guideline Q3A is the representative one. In this guideline, at the time of approving a drug, the amount of each related compound in the drug is limited up to 0.1% or 0.2%, etc. and information such as toxicity-related data, etc., which should be provided, is discriminately applied according to the related compound exceeding the limit. This implies that since it is unknown how a related compound of a drug would act in vivo, the amount of the related compound must be reduced in the procedure of manufacturing the drug. Therefore, a manufacturing process for reducing the related compounds and setting of the upper limit to amount according to the characteristics (structure and toxicity) of each related compound are essential factors in quality control of the drug.

CONTENTS OF THE INVENTION

Problems to be Solved

One purpose of the present invention is to provide a polymeric micelle-type pharmaceutical composition of poorly water-soluble drug comprising an amphiphilic block copolymer, which contains a specific related compound in an amount within a specified limit.

The other purpose of the present invention is to provide a method for preparing said pharmaceutical composition.

Technical Means to Solve the Problems

One aspect of the present invention provides a polymeric micelle pharmaceutical composition, comprising: a purified amphiphilic block copolymer comprising a hydrophilic block (A) and a hydrophobic block (B), and one or more poorly water-soluble drugs selected from the group consisting of paclitaxel and docetaxel, wherein the pharmaceutical composition contains, when stored at 40° C. for 6 months, a related compound represented by the following Formula 1 in an amount of less than 0.58 part by weight, based on 100 parts by weight of the initial amount of the poorly water-soluble drug:

[Formula 1]

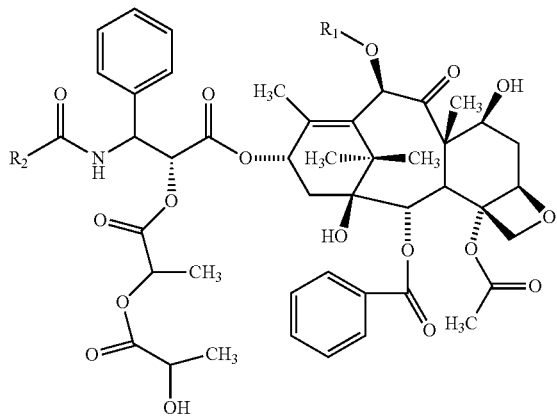

wherein
$R_1$ is H or $COCH_3$, and $R_2$ is phenyl or $OC(CH_3)_3$.

Another aspect of the present invention provides a method for preparing a polymeric micelle pharmaceutical composition, comprising: (a) purifying an amphiphilic block copolymer comprising a hydrophilic block (A) and a hydrophobic block (B); (b) dissolving one or more poorly water-soluble drugs selected from the group consisting of paclitaxel and docetaxel, and the purified amphiphilic block copolymer in an organic solvent; and (c) adding an aqueous solvent to the solution obtained in step (b) to form polymeric micelles; wherein the pharmaceutical composition contains, when stored at 40° C. for 6 months, a related compound represented by the above Formula 1 in an amount of less than 0.58 part by weight, based on 100 parts by weight of the initial amount of the poorly water-soluble drug.

Effects of the Invention

According to the present invention, a pharmaceutical composition of poorly water-soluble drug, which has reduced related compounds and improved storage stability, can be obtained.

BRIEF EXPLANATION OF THE DRAWINGS

FIG. 1 is the resulting chromatogram of HPLC analysis for the polymeric micelle composition containing paclitaxel used in Experimental Example 1-1, which had been subjected to the six-month acceleration test.

FIG. 2 is the resulting chromatogram and spectrum of LC/MS/MS analysis conducted in Experimental Example 1-2 for the related compound isolated in Experimental Example 1-1:
(a) RRT 1.10±0.02 (1.08~1.12) (hereinafter, RRT 1.10 is used interchangeably with RRT 1.10±0.02)
(b) RRT 1.12±0.02 (1.10~1.14) (hereinafter, RRT 1.12 is used interchangeably with RRT 1.12±0.02)

FIG. 3 is the resulting chromatogram of HPLC analysis for the induced reaction product obtained in Experimental Example 2:

(a) Polymeric micelle pharmaceutical composition containing paclitaxel
(b) Paclitaxel
(c) Reaction product of paclitaxel and L-lactide
(d) Reaction product of paclitaxel and D-lactide FIG. 4 is the resulting chromatogram of LC/MS/MS analysis for the induced reaction product obtained in Experimental Example 3:
(a) Paclitaxel
(b) Reaction product of paclitaxel and L-lactide
(c) Reaction product of paclitaxel and D-lactide FIG. 5 is the resulting chromatogram of HPLC analysis conducted in Experimental Example 4.

DETAILED DESCRIPTION TO CARRY OUT THE INVENTION

The present invention is explained in more detail below.

The pharmaceutical composition of an embodiment of the present invention comprises a purified amphiphilic block copolymer comprising a hydrophilic block (A) and a hydrophobic block (B).

According to one embodiment of the present invention, the amphiphilic block copolymer comprises an A-B type diblock copolymer consisting of a hydrophilic block (A) and a hydrophobic block (B), or a B-A-B type triblock copolymer.

According to one embodiment of the present invention, the amphiphilic block copolymer may comprise the hydrophilic block in an amount of 20 to 95% by weight, and more concretely 40 to 95% by weight, based on the total weight of the copolymer. In addition, the amphiphilic block copolymer may comprise the hydrophobic block in an amount of 5 to 80% by weight, and more concretely 5 to 60% by weight, based on the total weight of the copolymer.

According to one embodiment of the present invention, the amphiphilic block copolymer may have a number average molecular weight of 1,000 to 50,000 Daltons, and more concretely 1,500 to 20,000 Daltons.

According to one embodiment of the present invention, the hydrophilic block is a polymer having biocompatibility and may comprise one or more selected from the group consisting of polyethylene glycol or derivatives thereof, polyvinylpyrrolidone, polyvinyl alcohol, polyacrylamide and combinations thereof, and more concretely, it may comprise one or more selected from the group consisting of polyethylene glycol, monomethoxypolyethylene glycol and combinations thereof. The hydrophilic block may have a number average molecular weight of 200 to 20,000 Daltons, and more concretely 200 to 10,000 Daltons.

According to one embodiment of the present invention, the hydrophobic block is a polymer having biodegradability and may be a polymer of monomers derived from alpha (α)-hydroxy acid. Concretely, it may comprise one or more selected from the group consisting of polylactide, polyglycolide, polymandelic acid, polycaprolactone, polydioxan-2-one, polyamino acid, polyorthoester, polyanhydride, polycarbonate and combinations thereof, and more concretely, it may comprise one or more selected from the group consisting of polylactide, polyglycolide, polycaprolactone, polydioxan-2-one and combinations thereof. The hydrophobic block may have a number average molecular weight of 200 to 20,000 Daltons, and more concretely 200 to 10,000 Daltons.

According to one embodiment of the present invention, an amphiphilic block copolymer comprising a hydrophobic polymer block of poly(alpha (α)-hydroxy acid) may be synthesized by a known ring-opening polymerization method using a hydrophilic polymer having hydroxyl group as an initiator, and a lactone monomer of alpha (α)-hydroxy acid. For example, L-lactide or D,L-lactide may be polymerized with hydrophilic polyethylene glycol or monomethoxypolyethylene glycol having hydroxyl group as an initiator by ring-opening. Synthesis of diblock or triblock copolymer is possible according to the number of hydroxyl group existing in the hydrophilic block which is the initiator. In the ring-opening polymerization, an organometallic catalyst such as tin oxide, lead oxide, tin octoate, antimony octoate, etc. may be used, and tin octoate having biocompatibility is preferably used in preparing polymer for medical use.

In an embodiment of the present invention, as the amphiphilic block copolymer, a purified one is used. According to a preferable embodiment of the present invention, the amphiphilic block copolymer is one that has been purified by sublimation.

The purification by sublimation may be conducted at a temperature of preferably 80° C. or higher and lower than 120° C. and more preferably 80 to 100° C., and under a pressure of a vacuum degree of preferably 10 torr or less, more preferably 5 torr or less and even more preferably 1 torr or less, for a time of preferably 10 to 74 hours, more preferably 10 to 48 hours and even more preferably 24 to 48 hours. Conducting the purification by sublimation under such conditions can minimize the change in molecular weight of the copolymer and remove impurities therefrom.

The pharmaceutical composition of an embodiment of the present invention comprises, as active ingredient, one or more poorly water-soluble drugs selected from the group consisting of paclitaxel and docetaxel.

According to one embodiment of the present invention, the pharmaceutical composition may further comprise, as additional active ingredient, one or more poorly water-soluble drugs other than paclitaxel and docetaxel. As such an additional active ingredient, one or more taxane anticancer agents selected from the group consisting of 7-epipaclitaxel, t-acetylpaclitaxel, 10-desacetylpaclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel and cabazitaxel, may be used.

The pharmaceutical composition of an embodiment of the present invention may comprise the poorly water-soluble drug in an amount of 0.1 to 50 parts by weight, and more concretely 0.5 to 30 parts by weight, based on 100 parts by weight of the amphiphilic block copolymer. If the amount of the poorly water-soluble drug is too small as compared with that of the amphiphilic block copolymer, the weight ratio of the amphiphilic copolymer used per drug is high and thus the time for reconstitution may increase. On the other hand, if the amount of the poorly water-soluble drug is too large, there may be a problem of rapid precipitation of the poorly water-soluble drug.

As used herein, the "initial" amount of the poorly water-soluble drug means the weight of the poorly water-soluble drug incorporated when the pharmaceutical composition was prepared.

In an embodiment of the present invention, the pharmaceutical composition contains, when stored at the accelerated condition (40° C.) for 6 months, a related compound represented by the following Formula 1 in an amount of less than 0.58 part by weight, based on 100 parts by weight of the initial amount of the poorly water-soluble drug:

[Formula 1]

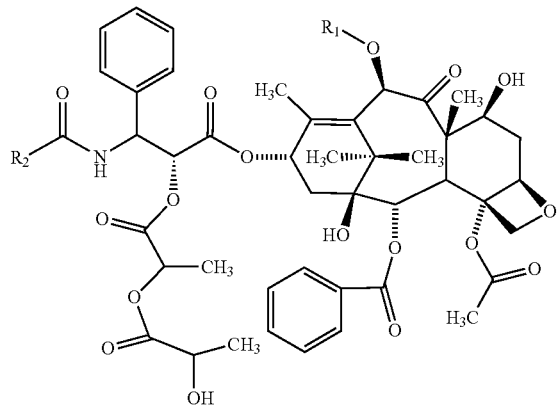

wherein $R_1$ is H or $COCH_3$, and $R_2$ is phenyl or $OC(CH_3)_3$.

The compound of Formula 1 may include a compound of the following Formula 1a, a compound of the following Formula 1b, or both of them:

[Formula 1a]

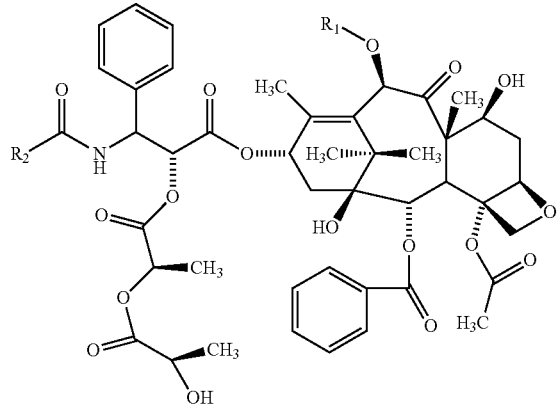

[Formula 1b]

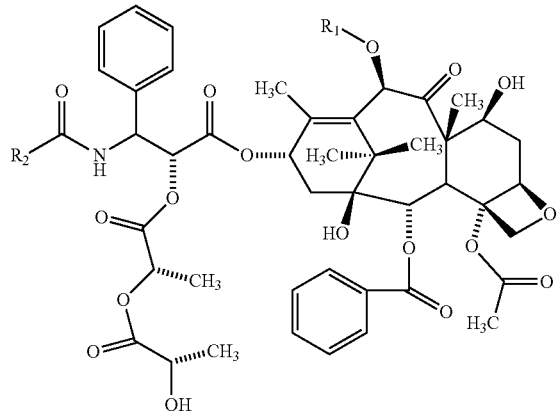

In the above Formulas 1a and 1b, $R_1$ and $R_2$ are the same as defined in Formula 1 above.

According to one embodiment of the present invention, the poorly water-soluble drug is paclitaxel, and the related compound(s) may include the compound represented by the following Formula 1c:

[Formula 1c]

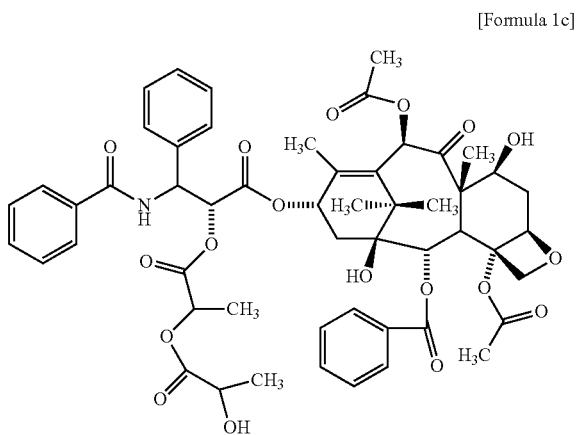

The compound of Formula 1c may include the compound of the following Formula 1d, the compound of the following Formula 1e, or both of them:

[Formula 1d]

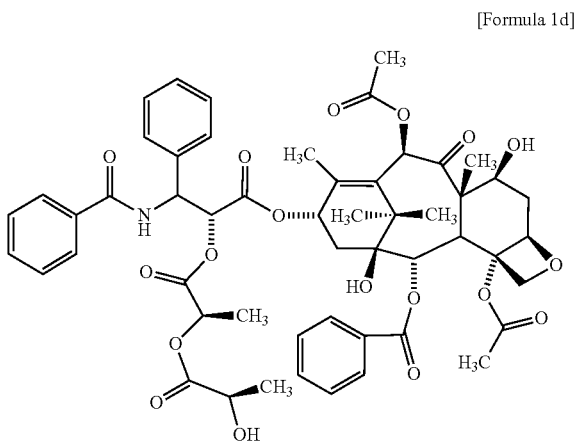

[Formula 1e]

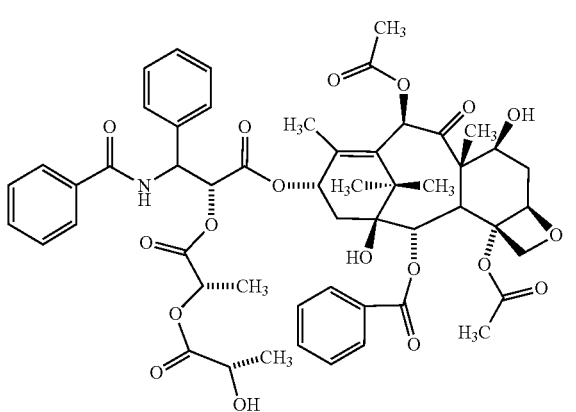

The pharmaceutical composition of an embodiment of the present invention may contain, when stored at the accelerated condition (40° C.) for 6 months, a related compound of Formula 1 (particularly, Formula 1c) in an amount of less than 0.58 part by weight, for example, 0.5 part by weight or less, preferably 0.35 part by weight or less, more preferably 0.2 part by weight or less, even more preferably 0.1 part by weight or less, and most preferably 0.07 part by weight or less, based on 100 parts by weight of the initial amount of the poorly water-soluble drug.

The pharmaceutical composition of an embodiment of the present invention may contain, when stored at the accelerated condition (40° C.) for 6 months, a related compound of Formula 1a (particularly, Formula 1d) in an amount of less than 0.22 part by weight, for example, 0.2 part by weight or less, preferably 0.15 part by weight or less, more preferably 0.1 part by weight or less, even more preferably 0.06 part by weight or less, and most preferably 0.05 part by weight or less, based on 100 parts by weight of the initial amount of the poorly water-soluble drug.

The pharmaceutical composition of an embodiment of the present invention may contain, when stored at the accelerated condition (40° C.) for 6 months, a related compound of Formula 1b (particularly, Formula 1e) in an amount of less than 0.36 part by weight, for example, 0.3 part by weight or less, preferably 0.2 part by weight or less, more preferably 0.1 part by weight or less, even more preferably 0.04 part by weight or less, and most preferably 0.02 part by weight or less, based on 100 parts by weight of the initial amount of the poorly water-soluble drug.

The pharmaceutical composition of an embodiment of the present invention may contain, when stored at the severe condition (80° C.) for 3 weeks, a related compound of Formula 1 (particularly, Formula 1c) in an amount of less than 0.45 part by weight, preferably 0.4 part by weight or less, more preferably 0.2 part by weight or less, and most preferably 0.16 part by weight or less, based on 100 parts by weight of the initial amount of the poorly water-soluble drug.

The pharmaceutical composition of an embodiment of the present invention may contain, when stored at the severe condition (80° C.) for 3 weeks, a related compound of Formula 1a (particularly, Formula 1d) in an amount of less than 0.18 part by weight, preferably 0.15 part by weight or less, more preferably 0.1 part by weight or less, and most preferably 0.08 part by weight or less, based on 100 parts by weight of the initial amount of the poorly water-soluble drug.

The pharmaceutical composition of an embodiment of the present invention may contain, when stored at the severe condition (80° C.) for 3 weeks, a related compound of Formula 1b (particularly, Formula 1e) in an amount of less than 0.27 part by weight, preferably 0.2 part by weight or less, more preferably 0.1 part by weight or less, and most preferably 0.08 part by weight or less, based on 100 parts by weight of the initial amount of the poorly water-soluble drug.

In an embodiment of the present invention, the pharmaceutical composition, which contains a specific related compound in an amount within a specified limit, is a commercially available composition since it can be produced on a large scale.

In an embodiment, the pharmaceutical composition of the present invention does not have ether, for example, diethyl ether, at all.

In an embodiment, the pharmaceutical composition of the present invention does not have metal salt, for example, alkali metal salt and/or salt for salting out, for example, NaCl or KCl, at all.

The pharmaceutical composition of an embodiment of the present invention can be prepared by a method comprising (a) purifying an amphiphilic block copolymer comprising a hydrophilic block (A) and a hydrophobic block (B); (b) dissolving one or more poorly water-soluble drugs selected from the group consisting of paclitaxel and docetaxel, and the purified amphiphilic block copolymer in an organic solvent; and (c) adding an aqueous solvent to the solution obtained in step (b) to form polymeric micelles.

The purification of the amphiphilic block copolymer is explained above, and a conventional method can be used for the formation of the polymeric micelles.

In the method for preparing a pharmaceutical composition of an embodiment of the present invention, as the organic solvent, a water-miscible organic solvent, for example, selected from the group consisting of alcohol (for example, ethanol), acetone, tetrahydrofuran, acetic acid, acetonitrile and dioxane and combinations thereof can be used, but it is not limited thereto. In addition, as the aqueous solvent, one selected from the group consisting of conventional water, distilled water, distilled water for injection, physiological saline, 5% glucose, buffer and combinations thereof can be used, but it is not limited thereto.

The method for preparing a pharmaceutical composition of an embodiment of the present invention may further comprise removing an organic solvent after said step (a).

In an embodiment, the method may further comprise lyophilizing the micelle composition with addition of a lyophilization aid. The lyophilization aid may be added for the lyophilized composition to maintain a cake form. In another embodiment, the lyophilization aid may be one or more selected from the group consisting of sugar and sugar alcohol. The sugar may be one or more selected from lactose, maltose, sucrose or trehalose. The sugar alcohol may be one or more selected from mannitol, sorbitol, maltitol, xylitol and lactitol. The lyophilization aid may also function to facilitate homogeneous dissolution of the lyophilized polymeric micelle composition upon reconstitution. The lyophilization aid may be contained at an amount of 1 to 90 weight %, particularly, 1 to 60 weight %, more particularly 10 to 60 weight %, based in a total weight of the lyophilized composition.

The present invention is explained in more detail by the following examples. However, these examples seek to illustrate the present invention only, and the scope of the present invention is not limited by the examples in any manner.

EXAMPLES

Preparation Example 1: Synthesis of Diblock Copolymer Consisting of Monomethoxypolyethylene Glycol and D,L-Lactide (mPEG-PDLLA) and Purification by Sublimation Method 150 g of monomethoxypolyethylene glycol (mPEG, number average molecular weight=2,000) was fed into a 500-ml round-bottom flask equipped with an agitator, and agitated at 120° C. under vacuum condition for 2 hours to remove moisture. 0.15 g of tin octoate ($Sn(Oct)_2$) dissolved in 200 μl of toluene was added in the reaction flask, and further agitated under vacuum condition for 1 hour to distill and remove toluene. 150 g of D,L-lactide was then added and agitated under nitrogen atmosphere for dissolution. After D,L-lactide was dissolved completely, the reactor was tightly sealed and the polymerization reaction was conducted at 120° C. for 10 hours. After the reaction was terminated, under agitation with a magnetic bar, the reactor was connected to a vacuum pump and the product was purified under a pressure of 1 torr or less by a sublimation method for 7 hours to obtain 262 g of mPEG-PDLLA in molten state. The molecular weight (Mn: ~3740) was calculated by analyzing with $^1$H-NMR obtaining relative intensities of appropriate peaks with reference to —$OCH_3$ which is the terminal group of monomethoxypolyethylene glycol.

Preparation Example 2: Purification of Diblock Copolymer (mPEG-PDLLA) by Sublimation Method 30 g of mPEG-PDLLA, which was obtained in the polymerization reaction process of Preparation Example 1 before conducting the purification process, was fed into a one-necked flask and dissolved at 80° C. Under agitation with a magnetic bar, the reactor was connected to a vacuum pump and the product was purified under a pressure of 1 torr or less by a sublimation method for 24 hours and 48 hours.

Preparation Example 3: Purification of Diblock Copolymer (mPEG-PDLLA) by Sublimation Method Except that the purification temperature was 100° C., the purification was conducted by the same method as in Preparation Example 2.

Preparation Example 4: Purification of Diblock Copolymer (mPEG-PDLLA) by Sublimation Method Except that the purification temperature was 120° C., the purification was conducted by the same method as in Preparation Example 2.

Preparation Example 5: Purification of Diblock Copolymer (mPEG-PDLLA) by Adsorption Method Using Aluminum Oxide ($Al_2O_3$)

30 g of mPEG-PDLLA, which was obtained in the polymerization reaction process of Preparation Example 1 before conducting the purification process, was fed into a one-necked flask and dissolved by adding acetone (60 ml). Aluminum oxide (15 g) was added thereto and completely mixed. The one-necked flask was connected to a rotary evaporator, and the contents were mixed at 50° C. at 60 rpm for 2 hours. The solution was then filtered at room temperature with PTFE filter paper (1 μm) to remove aluminum oxide. The filtered acetone solution was distilled using a rotary evaporator at 60° C. under vacuum to remove acetone, thereby to obtain the purified mPEG-PDLLA. The molecular weight (Mn: ~3690) was calculated by analyzing with $^1$H-NMR obtaining relative intensities of appropriate peaks with reference to —$OCH_3$ which is the terminal group of monomethoxypolyethylene glycol.

The molecular weight change of mPEG-PDLLA according to the purification conditions in the above Preparation Examples 2 to 5 is shown in the following Table 1.

TABLE 1

|  | Purification Temperature (° C.) | Purification Time (hr) | Molecular weight (Mn) |
|---|---|---|---|
| Preparation Example 2 | 80 | 24 | 3740 |
|  |  | 48 | 3740 |
| Preparation | 100 | 24 | 3720 |

TABLE 1-continued

| | Purification Temperature (° C.) | Purification Time (hr) | Molecular weight (Mn) |
|---|---|---|---|
| Example 3 | | 48 | 3700 |
| Preparation Example 4 | 120 | 24 | 3650 |
| | | 48 | 3550 |
| Preparation Example 5 | Al$_2$O$_3$ purification | | 3690 |

From the results of Table 1, it can be seen that the reduced amount of the molecular weight of mPEG-PDLLA increases as the purification temperature becomes higher. The purification condition of 80 to 100° C. and 24 to 48 hours, particularly 100° C. and 24 hours, can be thought of as efficient.

Comparative Example 1: Preparation of Polymeric Micelle Composition Containing Paclitaxel 1 g of paclitaxel and 5 g of mPEG-PDLLA obtained in Preparation Example 1 were weighed, and 4 ml of ethanol was added thereto and agitated at 60° C. until the mixture was completely dissolved to form a clear solution. Ethanol was then removed by distillation under reduced pressure using a rotary evaporator equipped with a round-bottom flask at 60° C. for 3 hours. The temperature was then lowered to 50° C., and 140 ml of distilled water at room temperature was added and reacted until the solution became clear in blue color to form polymeric micelles. As a lyophilization aid, 2.5 g of anhydrous lactose was added thereto and dissolved completely, filtered using a filter with a pore size of 200 nm, and freeze-dried to obtain a polymeric micelle composition containing paclitaxel in powder form.

Example 1: Preparation of Polymeric Micelle Composition Containing Paclitaxel Except that mPEG-PDLLA purified for 24 hours in Preparation Example 3 was used, a polymeric micelle composition containing paclitaxel was prepared by the same method as in Comparative Example 1.

Example 2: Preparation of Polymeric Micelle Composition Containing Paclitaxel Except that mPEG-PDLLA purified in Preparation Example 5 was used, a polymeric micelle composition containing paclitaxel was prepared by the same method as in Comparative Example 1.

Experimental Example 1-1: Isolation of Related Compound by Liquid Chromatography To a vial containing 100 mg of polymeric micelle composition containing paclitaxel, which had been subjected to the six-month acceleration test (temperature: 40° C.), 16.7 ml of deionized water (DW) was fed and the contents were completely dissolved, and the total amount of the liquid was taken and transferred to a 20-ml volumetric flask, and the marked line was met to make the total volume 20 ml (5.0 mg/ml). 2 ml of this liquid was taken and transferred to a 10-ml volumetric flask, and the marked line was met with acetonitrile to make the total volume 10 ml (1 mg/ml). For the above composition, related compound was isolated and fractionally collected using the following liquid chromatography.

Conditions for Liquid Chromatography
1) Column: Poroshell 120 PFP (4.6×150 mm, 2.7 μm, Agilent)
2) Mobile phase: A: DW/B: Acetonitrile

| Time (min) | % A | % B |
|---|---|---|
| 0.00 | 65 | 35 |
| 25.00 | 45 | 55 |
| 28.00 | 45 | 55 |
| 30.00 | 65 | 35 |
| 35.00 | 65 | 35 |

3) Flow rate: 0.6 ml/min
4) Injection volume: 10 μl
5) Detector: UV absorption spectrophotometer (Measurement wavelength: 227 nm)

The resulting chromatogram of HPLC analysis is shown in FIG. 1.

Experimental Example 1-2: Qualitative Analysis of Related Compounds Using LC/MS/MS The related compounds isolated in Experimental Example 1-1 (RRT: 1.10±0.02 (1.08~1.12) and 1.12±0.02 (1.10~1.14)) were qualitatively analyzed by MS scan of liquid chromatography-mass spectrometer (LC/MS/MS). As the LC/MS/MS, liquid chromatography 1200 series and electrospray ionization mass spectrometer 6400 series (Agilent, US) were used. The conditions for analysis were as follows.

Conditions for Liquid Chromatography
1) Column: Cadenza HS-C18 (3.0×150 mm, 3 μm, Imtakt)
2) Mobile phase: A: 0.5 mM ammonium acetate with 0.03% acetic acid/B: Acetonitrile

| Time (min) | % A | % B |
|---|---|---|
| 0.00 | 80 | 20 |
| 4.00 | 55 | 45 |
| 9.00 | 55 | 45 |
| 9.10 | 80 | 20 |
| 15.00 | 80 | 20 |

3) Flow rate: 0.4 ml/min
4) Injection volume: 2 μl
5) Detector: UV absorption spectrophotometer (Measurement wavelength: 227 nm)

Conditions for Electrospray Ionization Mass Spectrometer
1) Ionization: Electrospray Ionization, Positive (ESI+)
2) MS Method: MS2 scan/Product ion scan
3) Ion source: Agilent Jet Stream ESI
4) Nebulizer gas (pressure): Nitrogen (35 psi)
5) Ion spray voltage: 3500 V
6) Drying gas temperature (flow rate): 350° C. (7 L/min)
7) Sheath gas temperature (flow rate): 400° C. (10 L/min)
8) Fragmentor: 135 V
9) Nozzle voltage: 500 V
10) Cell accelerator voltage: 7 V
11) EMV: 0 V
12) Collision energy: 22 V
13) Precursor ion: m/z 1020.2
14) Mass scan range: m/z 100~1500

The substance for analysis, which was isolated and came out of the detection stage, was set to flow in the mass spectrometer, and at that time the detected ion of related compound was qualitatively analyzed selecting the characteristic ion of mass spectrum [M+Na].

The resulting spectrum of LC/MS/MS analysis is shown in FIG. 2.

Experimental Example 2: Induction of Reaction of Paclitaxel and Lactide and HPLC Analysis of Reaction Product In the related compounds which were fractionally collected from the polymeric micelle composition containing paclitaxel in Experimental Example 1-1, many polymers existed together and thus direct experiment was very difficult. As a result of the qualitative analysis through Experimental Example 1-2, the related compounds at RRT 1.10 and 1.12 positions were presumed as compounds produced by combination of paclitaxel and lactide. Accordingly, an experiment of inducing a reaction by adding lactide to paclitaxel directly and analyzing the reaction product was carried out to confirm whether the presumed related compounds were produced.

First, each of 5 mg of paclitaxel and 3 mg of L-lactide/D-lactide was dissolved in 1 ml of acetonitrile (ACN): DW=70:30 (v/v) solution, and the solutions were then mixed. This solution was transferred to an LC vial and analyzed by HPLC. The resulting chromatogram of HPLC analysis is shown in FIG. 3.

As a result of analysis, the peaks which newly appeared from the reaction product of L-lactide/D-lactide and paclitaxel were exactly identical with the peaks of impurities shown at RRT 1.10 and 1.12 in HPLC analysis after the six-month acceleration test of the polymeric micelle pharmaceutical composition. Together with this, it could also be confirmed that the compound of the combination of paclitaxel and L-lactide eluted first on HPLC and the combination of paclitaxel and D-lactide eluted later. Furthermore, in case of experiment using the same amount, it could be confirmed that the combination of paclitaxel and D-lactide was formed more than the combination of paclitaxel and L-lactide. It could be known from this that the impurities appearing at RRT 1.10 and 1.12 positions from the polymeric micelle composition containing paclitaxel, which had been subjected to the six-month acceleration test, were the materials formed as a result of reacting paclitaxel with L-lactide and D-lactide, respectively.

Experimental Example 3: Analysis of Reaction Product of Paclitaxel and Lactide Using LC/MS/MS Using LC/MS/MS, a sample containing paclitaxel only was MS scanned first, and as a result thereof, m/z 854.2 amu which was [M+H]$^+$ and m/z 876.2 amu which was [M+Na]$^+$ appeared. After that, when L-lactide and D-lactide were added to paclitaxel, m/z 1020.0 amu, which was not shown in the sample containing paclitaxel only, appeared and it was confirmed that the intensity thereof continuously increased with the lapse of time. The resulting spectrum of LC/MS/MS analysis is shown in FIG. 4.

It could be confirmed again from this that the structure of the related compound obtained through Experimental Example 1-1 was the 1020.0 amu compound which was [M+Na]$^+$ produced by the combination of paclitaxel and lactide isomer.

From the results of Experimental Examples 2 and 3 and conventional knowledge of reaction in organic chemistry, it could be known that the related compound at RRT 1.10 and 1.12 of the polymeric micelle composition was the following compound produced by the combination of paclitaxel and (L/D-) lactide.

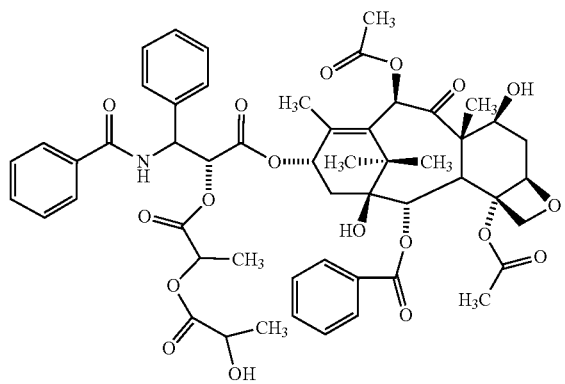

Combined form of paclitaxel and lactide: $C_{53}H_{59}NO_{18}$ (998.03 g/mol)

Experimental Example 4: Comparative Test of Storage Stability of Polymeric Micelle Containing Drug at Severe Condition (80° C.)

The polymeric micelle compositions of paclitaxel prepared in Comparative Example 1 and Examples 1 and 2 were kept in an oven at 80° C. for 3 weeks, and the compositions were then analyzed with HPLC to compare the amounts of related compound. The test solution was prepared by dissolving the micelle composition in 80% acetonitrile aqueous solution and diluting to 600 ppm concentration of paclitaxel. The resulting chromatogram of HPLC analysis is shown in FIG. 5 and the change in the amount of related compound (%) according to the severe test time is shown in the following Table 2.

HPLC Conditions

Column: Diameter 2.7 μm, poroshell 120PFP (4.6×150 mm, 2.7 μm) (Agilent column)

Mobile Phase

| Time (min) | Water:Acetonitrile |
|---|---|
| 0~25 | 65:35 → 45:55 |
| 25~28 | 45:55 |
| 28~30 | 45:55 → 65:35 |
| 30~35 | 65:35 |

Detector: UV absorption spectrophotometer (227 nm)

Flow rate: 0.6 ml/min

Amount of each related compound (%)=100(Ri/Ru)

Ri: Area of each related compound detected in test solution analysis

Ru: Sum of all peak areas detected in test solution analysis

TABLE 2

| Sample-Storage time | RRT* | | | | | |
|---|---|---|---|---|---|---|
| | 0.87 ± 0.02 (0.85~0.89) | 0.96 ± 0.02 (0.94~0.98) | 1.00 | 1.10 ± 0.02 (1.08~1.12) | 1.12 ± 0.02 (1.10~1.14) | 1.44 ± 0.05 (1.39~1.49) |
| Comparative Example 1-0 day(d) | 0.04% | 0.03% | 99.74% | — | — | — |
| Comparative Example 1-3 weeks(w) | 0.76% | 1.12% | 92.59% | 0.18% | 0.27% | 0.93% |
| Example 1-0 day(d) | 0.03% | 0.02% | 99.64% | 0.02% | — | — |
| Example 1-3 weeks(w) | 0.11% | 0.15% | 95.44% | 0.06% | 0.08% | 0.22% |
| Example 2-0 day(d) | — | 0.02% | 99.72% | — | — | — |
| Example 2-3 weeks(w) | 0.40% | 1.04% | 93.94% | 0.08% | 0.05% | 0.11% |

*RRT 0.87 ± 0.02: Paclitaxel, oxetane ring opened compound
RRT 0.96 ± 0.02: Paclitaxel, oxetane ring opened compound
RRT 1.00: Paclitaxel
RRT 1.10 ± 0.02: Paclitaxel, L-lactide reaction compound
RRT 1.12 ± 0.02: Paclitaxel, D-lactide reaction compound
RRT 1.44 ± 0.05: Paclitaxel, water eliminated compound From Table 2 and FIG. 5, it can be known that the stability of the polymeric micelle pharmaceutical composition of Example 1 or 2 was improved as compared with the composition of Comparative Example 1 and the reduction of paclitaxel amount was relatively smaller, whereby the effect of the drug contained in the composition can be maintained more stably.

Experimental Example 5: Comparative Test of Storage Stability of Polymeric Micelle Containing Drug at Accelerated Condition (40° C.)

Except that the polymeric micelle composition of paclitaxel prepared in Comparative Example 1 and Example 1 respectively was kept in a stability tester at 40° C. for 6 months, the test was conducted by the same method as in Experimental Example 4. The change in the amount of related compound (%) according to the acceleration test time is shown in the following Table 3.

TABLE 3

| Sample-Storage time | RRT* | | | |
|---|---|---|---|---|
| | 0.87 ± 0.02 (0.85~0.89) | 1.10 ± 0.02 (1.08~1.12) | 1.12 ± 0.02 (1.10~1.14) | 1.44 ± 0.05 (1.39~1.49) |
| Comparative Example 1-6 months | 0.17% | 0.22% | 0.36% | 0.12% |
| Example 1-6 months | 0.04% | 0.05% | 0.02% | 0.04% |

The above test result shows an average value of the amounts of each related compound and paclitaxel in the test conducted for 3 or more polymeric micelle compositions of different batches.

Through Experimental Example 5, it has been proven that the composition of Example 1, if stored at the accelerated storage temperature (40° C.) for 6 months, has lower amount of related compound than the composition of Comparative Example 1.

The invention claimed is:

1. A method for preparing a pharmaceutical composition, comprising
   (a) purifying an amphiphilic block copolymer comprising a hydrophilic block (A) and a hydrophobic block (B);
   (b) dissolving one or more poorly water-soluble drugs selected from the group consisting of paclitaxel and docetaxel, and the purified amphiphilic block copolymer obtained in step (a) in an organic solvent; and
   (c) adding an aqueous solvent to the solution obtained in step (b) to form polymeric micelles,
   wherein the amphiphilic block copolymer is purified by sublimation,
   wherein the sublimation is conducted at a temperature condition of from 80° C. to 100° C. and under a pressure condition of a vacuum degree of 10 torr or less,
   wherein the hydrophilic block (A) is polyethylene glycol or monomethoxy polyethylene glycol, and the hydrophobic block (B) is polylactide, polyglycolide or a combination thereof; and
   wherein the pharmaceutical composition contains, when stored at 40° C. for 6 months, a related compound represented by the following Formula 1 in an amount of less than 0.58 part by weight, based on 100 parts by weight of the initial amount of the poorly water-soluble drug:

[Formula 1]

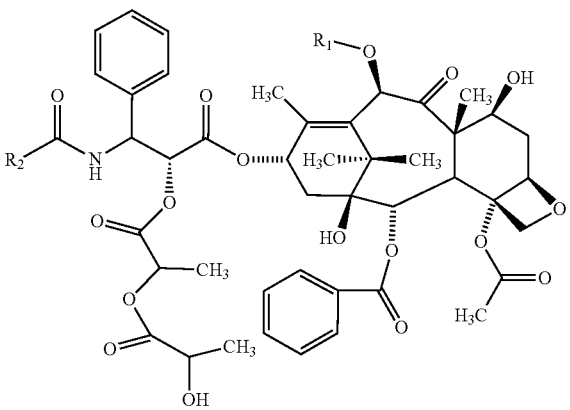

wherein
R$_1$ is H or COCH$_3$, and R$_2$ is phenyl or OC(CH$_3$)$_3$.

2. The method according to claim 1, wherein the purified amphiphilic block copolymer consists of a hydrophilic block (A) in an amount of 40 to 95% by weight and a hydrophobic block (B) in an amount of 5 to 60% by weight; and the hydrophobic block (B) has a number average molecular weight of 200 to 10,000 Daltons.

3. The method according to claim 1, wherein the compound of Formula 1 is a compound of the following Formula 1a and/or a compound of the following Formula 1b:

[Formula 1a]

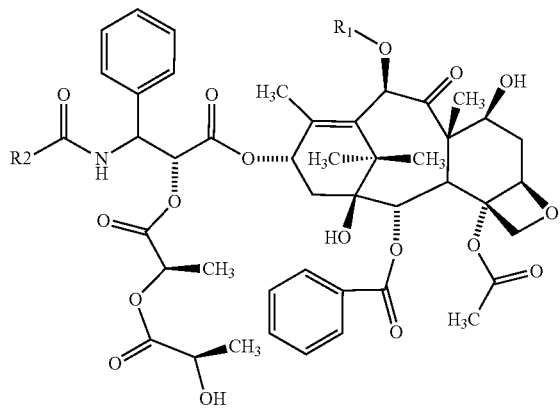

[Formula 1b]

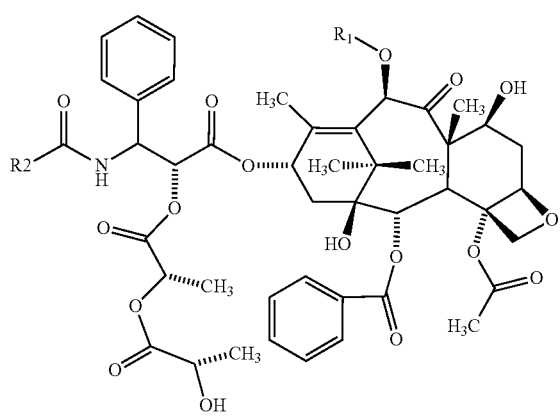

wherein $R_1$ and $R_2$ are the same as defined in claim 1.

4. The method according to claim 1, wherein the compound of Formula 1 is the compound of the following Formula 1c:

[Formula 1c]

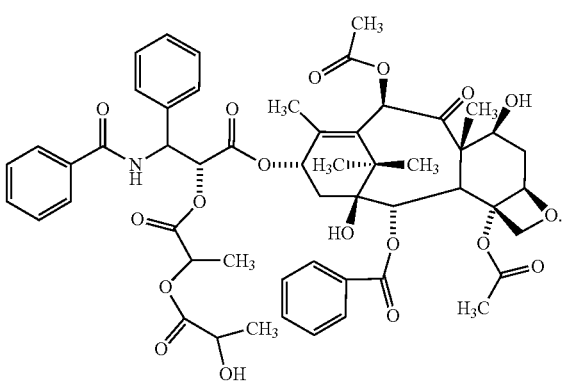

5. The method according to claim 4, wherein the compound of Formula 1c is the compound of the following Formula 1d and/or the compound of the following Formula 1e:

[Formula 1d]

[Formula 1e]

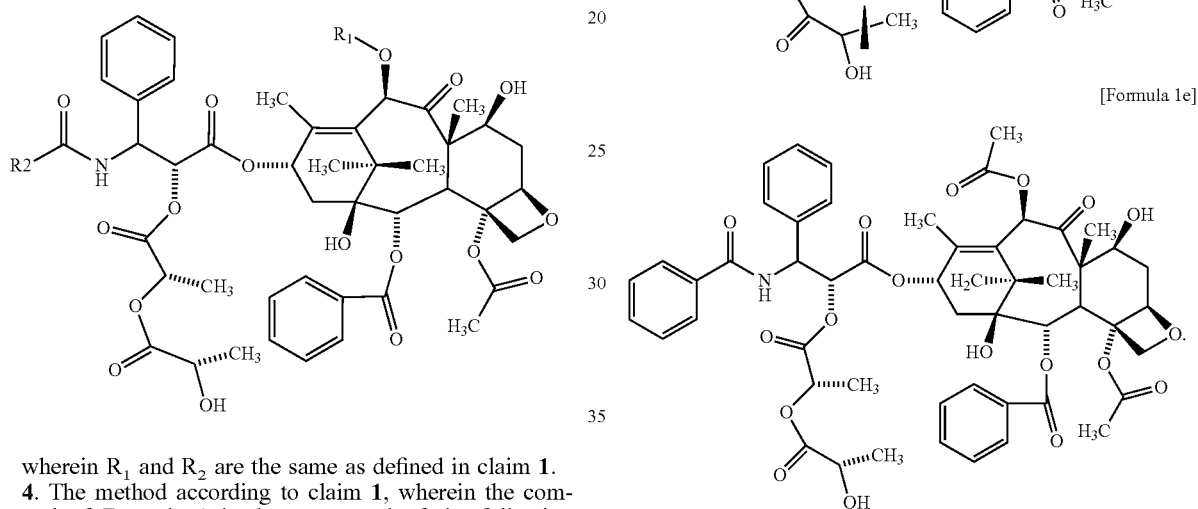

6. The method according to claim 1, wherein the organic solvent is a water-miscible organic solvent.

7. The method according to claim 6, wherein the water-miscible organic solvent is selected from the group consisting of alcohol, acetone, tetrahydrofuran, acetic acid, acetonitrile, dioxane and combinations thereof.

8. The method according to claim 1, wherein the pharmaceutical composition does not contain ether solvent.

9. The method according to claim 1, wherein the amphiphilic block copolymer has a number average molecular weight of 1,000 to 50,000 Daltons.

10. The method according to claim 1, wherein the amphiphilic block copolymer comprises an A-B type diblock copolymer consisting of a hydrophilic block (A) and a hydrophobic block (B), or a B-A-B type triblock copolymer.

11. The method according to claim 1, wherein the amphiphilic block copolymer comprises the hydrophilic block in an amount of 20 to 95% by weight, and the hydrophobic block in an amount of 5 to 80% by weight.

* * * * *